CHRYSANTHEMUM PLANT
Filed Jan. 29, 1971 2 Sheets-Sheet 1
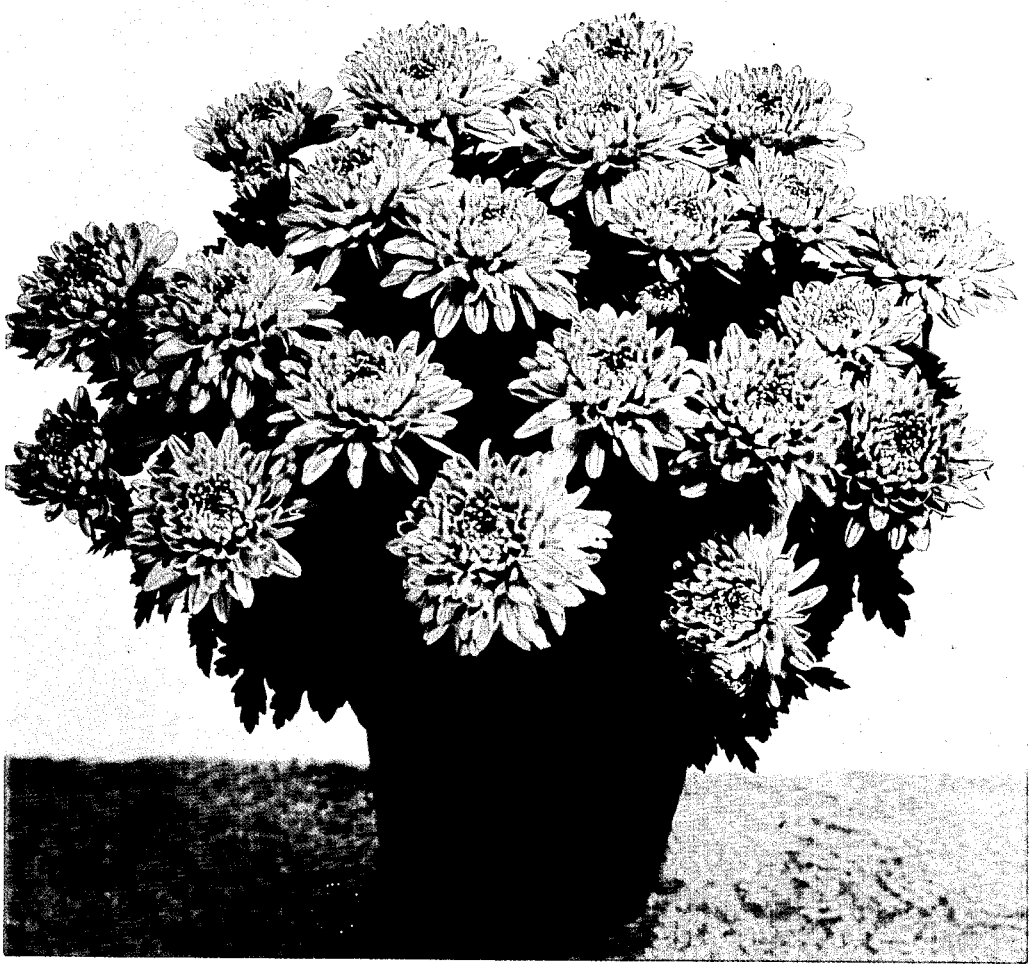
INVENTORS
WALTER H. JESSEL, JR.,
WILLIAM E. DUFFETT
BY Oberlin, Maky, Donnelly & Renner
ATTORNEYS CHRYSANTHEMUM PLANT
Filed Jan. 29, 1971 2 Sheets-Sheet 2
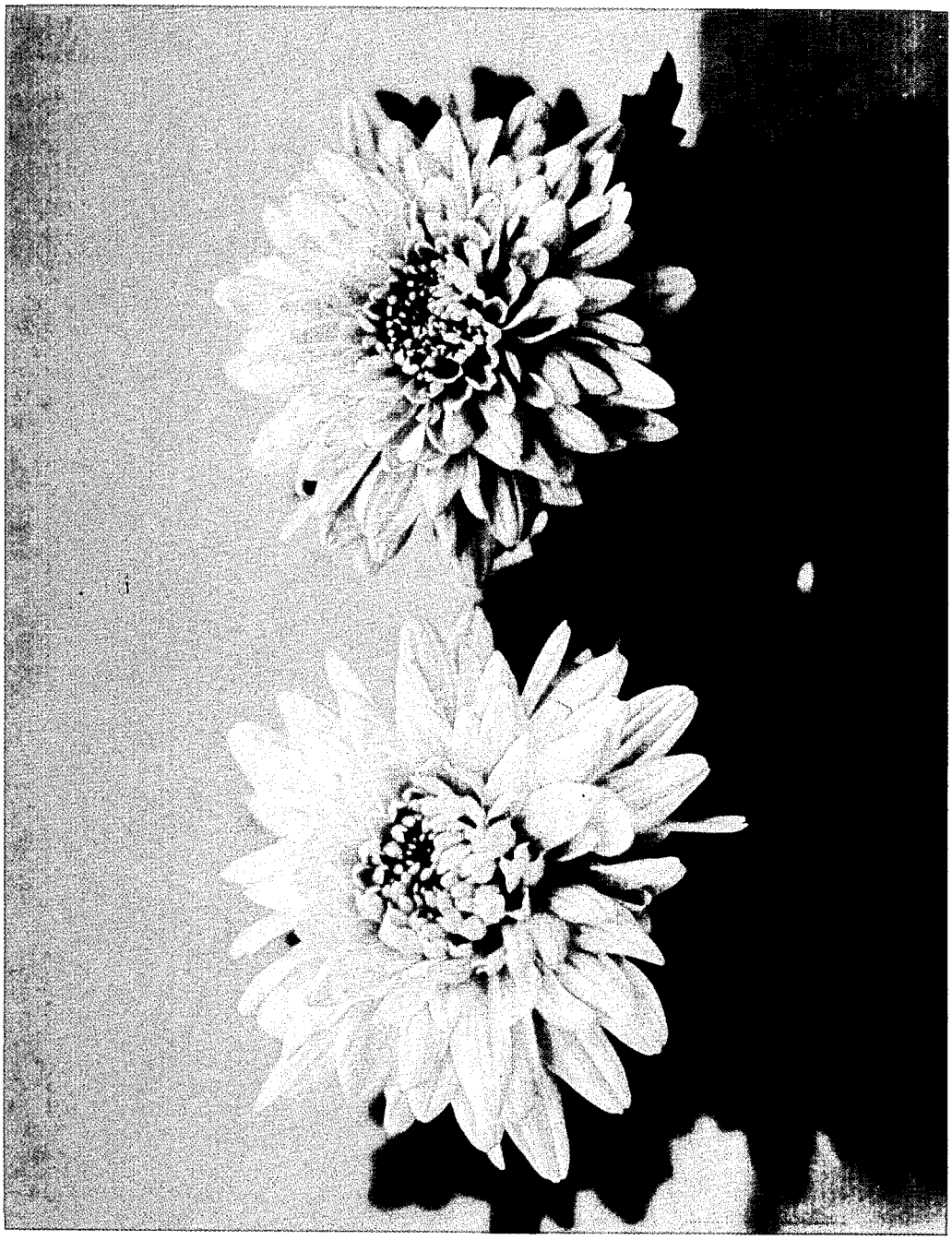
INVENTORS
WALTER H. JESSEL, JR.,
WILLIAM E. DUFFETT
BY
Oberlin, Maky, Donnelly & Renner
ATTORNEYS

United States Patent Office

Plant Pat. 3,256

Patented Aug. 15, 1972

3,256

CHRYSANTHEMUM PLANT

Walter H. Jessel, Jr., Doylestown, and William E. Duffett, Akron, Ohio, assignors to Yoder Brothers, Inc., Barberton, Ohio Filed Jan. 29, 1971, Ser. No. 111,159

Int. Cl. A01h *5/00*

U.S. Cl. Plt.—81 1 Claim

The present invention comprises a new and distinct cultivar of chrysanthemum plant which is a sport of the unpatented, but commercially well-known cultivar known in the United States as Snow Pink.

The new cultivar is similar in many respects to Deep Snow Pink, having the same characteristics of:

(1) Flower size.
(2) Flower form.
(3) Plant habit.
(4) Flowering response.
(5) Foliage color.

The new cultivar is distinguished from Snow Pink by its deeper lavender pink flower color. This deeper color is of particular significance during high light, high temperature periods when fading is a special problem. In such conditions a good lavender pink color is difficult to retain in the parent variety and other summer pink pot mums.

The new cultivar was selected from a flowering block of the parent cultivar in Barberton, Ohio. When a sexually reproduced by cuttings at Barberton, Ohio, the new cultivar was found to retain its distinctive characteristics through successive propagations.

The new cultivar when grown in the vicinity of Barberton, Ohio, has been a response period of approximately eight weeks, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering in the northern and western United States and coastal California is from January through December; in Florida, from December through April.

In the accompanying drawings Sheet 1 illustrates the new cultivar by itself, showing the unique color characteristic of the new cultivar, and Sheet 2 comprises a comparison photograph of the new cultivar and the cultivar Glo Pink, with the latter appearing on the left and the new cultivar on the right. The cultivar Glo Pink is also a sport of the cultivar Snow Pink, and is disclosed and claimed in our pending application Ser. No. 105,138, filed Jan. 8, 1971. The deep lavender color of the new cultivar is particularly noticeable in the comparison photograph.

In the following description, color references are to the Munsell Color Book, 1963 edition, and color comparisons have been made with the parent cultivar Snow Pink.

Botanical classification: Chrysanthemum morifolium.

Bloom:

*Size.*—3".
*Fully expanded.*—3½".

*Borne.*—Singly on disbudded shoots or clusters on non-disbudded shoots.
*Stems.*—Strong.
*Form.*—Decorative.
*Permanence.*—10 days.

| | Always Pink | Snow Pink |
|---|---|---|
| Color: | | |
| Center of flower | Dark Lavender 2.5RP4/2, dark Lavender 2.5RP5/2. | Lavender 2.5RP7/6. |
| Base of petals | Dark Lavender 2.5RP5/2, Lavender 2.5RP6/8. | Lavender 2.5RP7/6, Light Lavender 10P8/4. |
| Inside of petals | do | Do. |
| Reverse of petals | Lavender 2.5RP6/8, Lavender 2.5RP7/6. | Light Lavender 10P8/4, Pale Lavender 10P9/2. |
| Tonality from a distance. | Dark Lavender | Lavender. |
| Discoloration | Lavender | Light Lavender. |

Petals:
*Texture.*—Smooth.
*Appearance and form.*—Open at base, broaden quickly, shallow ridged quill-tapering to a blunt point.
*Arrangement.*—Composite, whorled on a single receptacle.
*Persistence.*—Resist shatter.
*Fragrance.*—Typical chrysanthemum.

Reproductive organs:
*Stamen, anthers.*—None to 5.
*Pollen.*—None to very scant.
*Arrangement.*—Clustered in center of flower, if present.
*Styles.*—Present both ray and disc florets.
*Length.*—short.
*Ovaries.*—At the base of petal attached to receptacle.

Plant:
*Form.*—Herbaceous.
*Growth.*—Semi-upright.
*Height.*—10½".
*Spread.*—Moderate.

Foliage:
*Top side.*—Green 10GY4/4.
*Size.*—4" long 2½" wide.
*Quantity.*—Numerous.
*Shape.*—Spatulate lobed.
*Texture.*—Smooth.
*Ribs and veins.*—Moderately prominent.
*Edge.*—Moderately indented.
*Serration.*—Slight.
*Underside.*—Light Green 7.5GY6/4.
*Stipules.*—Small.

We claim:

1. A new and distinct cultivar of chrysanthemum characterized particularly as to its uniqueness when compared to the cultivar Snow Pink by a deeper lavender pink flower color.

No references cited.

ROBERT E. BAGWILL, Primary Examiner

Disclaimer

Plant Pat. 3,256.—*Walter H. Jessel, Jr.*, Doylestown, and *William E. Duffett*, Akron, Ohio. CHRYSANTHEMUM PLANT. Patent dated Aug. 15, 1972. Disclaimer filed Aug. 23, 1973, by the assignee, *Yoder Brothers, Inc.*

Hereby disclaims the single claim of said patent.

[*Official Gazette December 11, 1973.*]